United States Patent
Yamada et al.

(10) Patent No.: US 9,611,233 B2
(45) Date of Patent: Apr. 4, 2017

(54) ORGANIC COMPOUND

(71) Applicant: CANON KABUSHIKI KAISHA, Tokyo (JP)

(72) Inventors: Kenji Yamada, Yokohama (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/014,921

(22) Filed: Feb. 3, 2016

(65) Prior Publication Data
US 2016/0152633 A1 Jun. 2, 2016

Related U.S. Application Data

(62) Division of application No. 14/368,471, filed as application No. PCT/JP2012/081221 on Nov. 26, 2012, now Pat. No. 9,284,328.

(30) Foreign Application Priority Data

Dec. 27, 2011 (JP) ................................. 2011-286778

(51) Int. Cl.
| | | |
|---|---|---|
| *C07D 277/24* | (2006.01) | |
| *G02F 1/15* | (2006.01) | |
| *C07D 333/16* | (2006.01) | |
| *C07D 495/04* | (2006.01) | |
| *C09K 9/02* | (2006.01) | |
| *C07D 277/28* | (2006.01) | |
| *G02F 1/00* | (2006.01) | |
| *G02F 1/155* | (2006.01) | |
| *G02F 1/163* | (2006.01) | |

(52) U.S. Cl.
CPC ......... *C07D 277/24* (2013.01); *C07D 277/28* (2013.01); *C07D 333/16* (2013.01); *C07D 495/04* (2013.01); *C09K 9/02* (2013.01); *G02F 1/0018* (2013.01); *G02F 1/15* (2013.01); *G02F 1/155* (2013.01); *G02F 1/163* (2013.01); *C09K 2211/1007* (2013.01); *C09K 2211/1037* (2013.01); *C09K 2211/1088* (2013.01); *C09K 2211/1092* (2013.01); *G02F 2001/1502* (2013.01); *G02F 2001/1515* (2013.01)

(58) Field of Classification Search
CPC ................................. C07D 277/24; G02F 1/15
See application file for complete search history.

(56) References Cited

U.S. PATENT DOCUMENTS

| | | | | |
|---|---|---|---|---|
| 7,471,437 B2* | 12/2008 | Lenhard | ............ | C09K 9/02 359/265 |
| 2012/0314272 A1* | 12/2012 | Yamada | ............... | C07D 495/14 359/265 |

* cited by examiner

*Primary Examiner* — Joseph Kosack
(74) *Attorney, Agent, or Firm* — Canon USA, Inc. IP Division (57) ABSTRACT

The present invention provides an organic compound to be used in an electrochromic device. The organic compound has excellent oxidation-reduction repeating characteristics and shows high transparency in the bleached state without showing light absorption in the visible light region. The organic compound has a structure represented by Formula [1] according to claim 1. In Formula [1], $A_1$ and $A_2$ represent substituents, and at least one of $A_1$ and $A_2$ is an alkyl group having 1 to 20 carbon atoms, an alkoxy group having 1 to 20 carbon atoms, or an optionally substituted aryl group. $R_1$ represents a substituent, X represents an electrochromic portion, and n is an integer of 1 to 3.

6 Claims, 2 Drawing Sheets

ORGANIC COMPOUND

CROSS REFERENCE TO RELATED APPLICATIONS

This application is a Divisional of U.S. patent application Ser. No. 14/368,471 filed Jun. 24, 2014, which is a National Stage Entry of PCT/JP2012/081221 filed Nov. 26, 2012, and which claims priority to Japanese Patent Application No. 2011-286778 filed Dec. 27, 2011, all of which are hereby incorporated by reference herein in their entireties.

TECHNICAL FIELD

The present invention relates to a novel electrochromic organic compound.

BACKGROUND ART

Various materials have been reported as electrochromic (hereinafter may be abbreviated as "EC") materials of which optical absorption properties (colored state and light transmittance) are changed by an electrochemical oxidation-reduction reaction.

Though metal oxides such as $WO_3$ are known as inorganic EC materials, the method of forming a film from such a metal oxide is limited to, for example, deposition, which disadvantageously prevents formation of a large-size film.

Organic EC materials are described in, for example, PTL 1 disclosing an EC device including a conductive polymer and PTL 2 disclosing an EC device including an organic low-molecular-weight compound such as viologen.

The conductive polymer described in PTL 1 can be directly formed as an EC layer on an electrode by electropolymerization of a monomer. As the conductive polymer that forms the EC layer, for example, polythiophene, polyaniline, and polypyrrole are known.

In these conductive polymers, the π-conjugated chain length of the main chain is changed by electrochemical oxidation or reduction of the polymer. This causes a change in the electronic state of the highest occupied molecular orbital (HOMO). As a result, the absorption wavelength of the conductive polymer is changed.

These conductive polymers in electrically neutral states absorb light in the visible light region. They, therefore, have colors. Oxidation of the conductive polymers shifts the absorption wavelengths to the longer wavelength side.

The absorption in the visible light region disappears by the shift of the absorption wavelength to the infrared region side, and thereby the EC device is bleached.

In the EC material of the viologen-based compound described in PTL 2, dications are dissolved in a solution in the bleached state, and viologen is converted into a radical cation state by a reduction reaction to deposit on an electrode and to have a color.

In PTL 1, though the stability is increased by delocalizing the unstable radical cation in its molecule, the stability is insufficient. Accordingly, repetition of oxidation and reduction deteriorates the material to decrease the performance of the EC device.

Furthermore, the conductive polymers absorb visible light in the electrically neutral state, i.e., the polymers have colors. Accordingly, if there is a portion in which the electrochemical reaction for discoloring is insufficient, remnant occurs to make it difficult to give high transparency.

The viologen-based EC organic compound in PTL 2 repeats deposition and dissolution and thereby causes a deterioration phenomenon.

This deterioration phenomenon is believed to be caused by insolubilization owing to irreversible crystallization or polymerization and to cause "remnant" in which transparency is not obtained even in the state for bleaching.

In addition, the viologen-based EC organic compound generates an unstable radical cation when reduced. Since the viologen-based EC organic compound does not have a mechanism for stabilizing the radical cation in the molecule, the radical cation is unstable. Accordingly, the durability of the device is low.

CITATION LIST

Patent Literature

PTL 1 Japanese Patent Laid-Open No. 56-67881
PTL 2 Japanese Patent Laid-Open No. 51-146253

SUMMARY OF INVENTION

The present invention provides an EC organic compound that shows high transparency in the bleached state and has high durability.

The organic compound is represented by the following Formula [1]:

[Chem. 1]

In Formula [1], $A_1$ and $A_2$ are each independently selected from the group consisting of hydrogen atoms, alkyl groups having 1 to 20 carbon atoms, alkoxy groups having 1 to 20 carbon atoms, and optionally substituted aryl groups, and at least one of $A_1$ and $A_2$ is selected from the alkyl groups, the alkoxy groups, and the aryl groups. The aryl groups each optionally have a substituent of an alkyl group having 1 to 4 carbon atoms or an alkoxy group having 1 to 4 carbon atoms.

Each $R_1$ independently represents a hydrogen atom, a halogen atom, an alkyl group having 1 to 20 carbon atoms, an alkoxy group having 1 to 20 carbon atoms, an alkyl ester group having 1 to 20 carbon atoms, an optionally substituted aryl group, an optionally substituted amino group, or a cyano group; and two or more $R_1$'s may be the same or different.

The aryl group optionally has a substituent of an alkyl group having 1 to 4 carbon atoms; n is an integer of 1 to 3; and X has a structure represented by any one of the following Formulae [2] to [4]. When n is 2 or 3, X's are each independently selected from the following Formulae [2] to [4].

[Chem. 2]

[Chem. 3]

[Chem. 4]

In Formulae [2] to [4], $R_2$, $R_3$, and $R_5$ are each independently selected from the group consisting of hydrogen atoms, halogen atoms, alkyl groups having 1 to 20 carbon atoms, alkoxy groups having 1 to 20 carbon atoms, optionally substituted aryl groups, alkyl ester groups having 1 to 20 carbon atoms, optionally substituted amino groups, and cyano groups; and $R_4$ represents an alkylene group having 1 to 20 carbon atoms.

DESCRIPTION OF EMBODIMENT

The present invention relates to an organic compound represented by the following Formula [1]:

[Chem. 5]

In Formula [1], $A_1$ and $A_2$ are each independently selected from the group consisting of hydrogen atoms, alkyl groups having 1 to 20 carbon atoms, alkoxy groups having 1 to 20 carbon atoms, and optionally substituted aryl groups; and at least one of $A_1$ and $A_2$ is selected from the alkyl groups, the alkoxy groups, and the aryl groups. The aryl groups each optionally have a substituent of an alkyl group having 1 to 4 carbon atoms or an alkoxy group having 1 to 4 carbon atoms.

Each $R_1$ independently represents a hydrogen atom, a halogen atom, an alkyl group having 1 to 20 carbon atoms, an alkoxy group having 1 to 20 carbon atoms, an alkyl ester group having 1 to 20 carbon atoms, an optionally substituted aryl group, an optionally substituted amino group, or a cyano group. The aryl group optionally has a substituent of an alkyl group having 1 to 4 carbon atoms; n is an integer of 1 to 3; and X has a structure represented by any one of Formulae [2] to [4] shown below. When n is 2 or 3, X's are each independently selected from Formulae [2] to [4].

The alkyl group having 1 to 20 carbon atoms represented by $A_1$ or $A_2$ may be linear, branched, or cyclic, and specific examples thereof include methyl, ethyl, n-propyl, isopropyl, n-butyl, t-butyl, pentyl, octyl, dodecyl, cyclohexyl, bicyclooctyl, and adamantyl groups.

The hydrogen atoms of the alkyl group may be partially or wholly substituted by fluorine atoms, for example, as a trifluoromethyl group.

From the viewpoint of easiness in synthesis, the alkyl group can be a methyl, ethyl, isopropyl, or t-butyl group, in particular, can be a methyl, ethyl, or isopropyl group.

Examples of the alkoxy group represented by $A_1$ or $A_2$ include methoxy, ethoxy, isopropoxy, n-butoxy, t-butoxy, ethylhexyloxy, octyloxy, and decyloxy groups.

Examples of the aryl group represented by $A_1$ or $A_2$ include phenyl, biphenyl, terphenyl, fluorenyl, naphthyl, fluoranthenyl, anthryl, phenanthryl, pyrenyl, and perylenyl groups. From the viewpoint of easiness in synthesis, the aryl group can be a phenyl or biphenyl group.

Examples of the optional substituent of the aryl group include halogen atoms, alkyl groups having 1 to 4 carbon atoms, alkoxy groups having 1 to 4 carbon atoms, aryl groups, aralkyl groups, substituted amino groups, and substituted silyl groups.

Specific examples of the alkyl groups, the alkoxy groups, and the aryl groups are the same as those of the alkyl, alkoxy, and aryl groups mentioned above as the substituents that may be introduced into $A_1$ or $A_2$. The hydrogen atoms of the alkyl group may be substituted by fluorine atoms.

At least one of $A_1$ and $A_2$ is selected from alkyl, alkoxy, and aryl groups. When at least one of $A_1$ and $A_2$ is selected from alkyl, alkoxy, and aryl groups, the other may be a hydrogen atom.

Examples of the alkyl, alkoxy, and aryl groups as the substituent represented by $R_1$ are the same as those of the alkyl, alkoxy, and aryl groups mentioned above as the substituents that may be introduced into $A_1$ or $A_2$.

Examples of the alkyl ester group having 1 to 20 carbon atoms represented by $R_1$ include methyl ester, ethyl ester, n-propyl ester, isopropyl ester, n-butyl ester, t-butyl ester, pentyl ester, isopentyl ester, t-amyl ester, hexyl ester, heptyl ester, octyl ester, ethylhexyl ester, cyclopentyl ester, and cyclohexyl ester groups.

Other examples of the substituents represented by $R_1$ include substituted amino groups such as dimethylamino and diphenylamino groups; and cyano groups.

Among these substituents, electron-donating substituents have an effect of increasing the electron density of the thiophene or thiazole moiety of the core. The electron donation of such a substituent decreases the oxidation potential to reduce the driving voltage when it used in an EC device and enhances the stability of the radical cation generated by oxidation.

Accordingly, in particular, the substituent represented by $R_1$ can be a group having high electron-donating properties such as a methyl, ethyl, methoxy, isopropoxy, or dimethylamino group.

Furthermore, among these substituents represented by $R_1$, polar substituents such as alkoxy groups and alkyl ester groups can increase solubility of the compound in polar solvents and, therefore, can be used particularly in EC devices having electrochromic layers and electrolyte layers as solution layers.

This is because that the contrast in the colored state can be enhanced by dissolving EC materials in the EC layer and the electrolyte layer at high concentrations. In particular, from this viewpoint, the substituent represented by $R_1$ can be a methyl ester, isopropyl ester, t-butyl ester, methoxy, or isopropoxy group.

The organic compound according to the present invention has a structure shown in Formula [1], i.e., a structure including a core portion represented by X composed of a thiophene or thiazole skeleton serving as a light-absorbing moiety and cage moiety each having a phenyl group having substituents at the ortho positions with respect to the core skeleton.

The structure of the phenyl group having substituents at the ortho positions to form the cage moiety will now be described.

The phenyl group has substituents at the ortho positions and can therefore prevent the core moiety from being in contact with other molecules.

The skeleton of the core moiety will now be described. In Formula [1], X representing the skeleton of the core moiety has a structure represented by any one of Formulae [2] to [4] shown below. When n is 2 or 3, X's are each independently selected from Formulae [2] to [4]. The structure represented by Formula [2] or [3] is constituted of a thiophene skeleton. The structure represented by Formula [4] is constituted of a thiazole skeleton.

[Chem. 6]

[2]

[Chem. 7]

[3]

[Chem. 8]

[4]

In Formulae [2] to [4], $R_2$, $R_3$, and $R_5$ are each independently selected from the group consisting of hydrogen atoms, halogen atoms, alkyl groups having 1 to 20 carbon atoms, alkoxy groups having 1 to 20 carbon atoms, optionally substituted aryl groups, alkyl ester groups having 1 to 20 carbon atoms, optionally substituted amino groups, and cyano groups; and $R_4$ represents an alkylene group having 1 to 20 carbon atoms.

Figure 1:
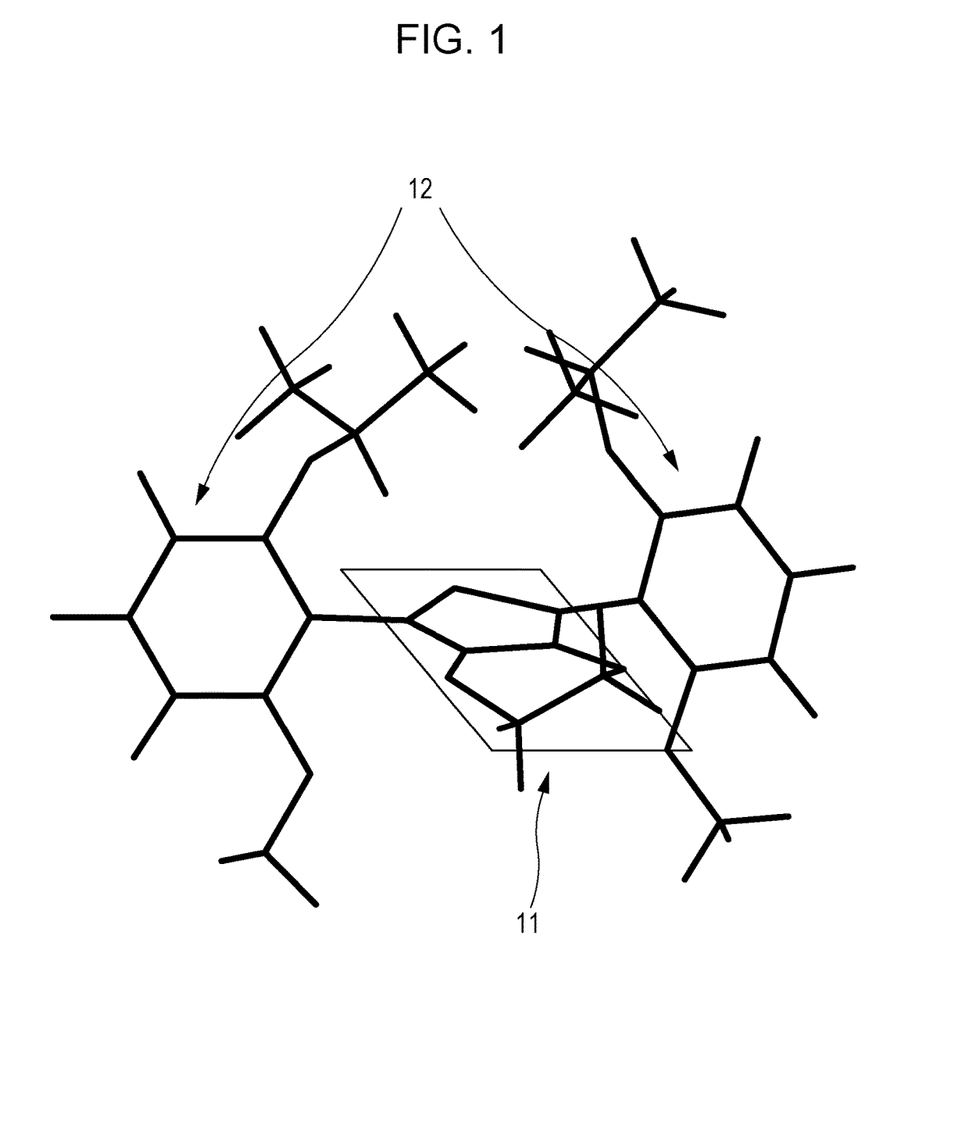
FIG. 1 is a diagram showing a molecular model of an example of the organic compound according to the present invention.

FIG. 1 is a diagram showing a molecular model of an example of the organic compound according to the present invention. The compound shown in FIG. 1 has the following chemical formula:

[Chem. 9]

FIG. 1 shows a steric structure of an organic compound molecule according to the present invention when $A_1$ or $A_2$ is an isopropoxy group or a methoxy group and X is 3,4-ethylenedioxythiophene.

In the steric structure shown in FIG. 1, the structural optimization calculation of the ground state was performed using electronic state calculation software, Gaussian 03*, Revision D.01. On this occasion, density functional theory was employed as the quantum-chemical computation, and B3LYP was used as the functional. In Gaussian 03, Revision D.01, 6-31G* was used as the base function.

*Gaussian 03, Revision D.01, M. J. Frisch, G. W. Trucks, H. B. Schlegel, G. E. Scuseria, M. A. Robb, J. R. Cheeseman, J. A. Montgomery, Jr., T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, C. Gonzalez, and J. A. Pople, Gaussian, Inc., Wallingford Conn., 2004.

In FIG. 1, the reference numeral 11 designates a 3,4-ethylenedioxythiophene plane, and the reference numeral 12 designates cage moieties each constituted of a phenyl group having an isopropoxy group and a methoxy group.

In this structure, the 3,4-ethylenedioxythiophene plane serving as the core moiety is prevented from coming into intermolecular contacts with other molecules by the cage moieties of the phenyl groups each having $A_1$ and $A_2$.

The plane of the core moiety represented by X lies in a plane that is approximately perpendicular to the cage moieties formed of the aromatic rings of the phenyl groups having $A_1$ and $A_2$.

Accordingly, the molecule has a shape such that the aromatic rings having substituents of bulky steric hindrance groups represented by $A_1$ and $A_2$ enclose the core moiety in which the radical cation is mainly generated. Thus, the phenyl groups have an effect (cage effect) of preventing the core moiety from being in contact with other molecules. The bulky steric hindrance groups can each have a structure that is more bulky than a methyl group for achieving the effect.

The structure represented by X serving as the core moiety of the organic compound according to the present invention is a light-absorbing moiety. The number of the thiophene ring or the thiazole ring represented by n in Formula [1] is one to three, and therefore the π-conjugated system is shorter than that of a conductive polymer. A shorter π-conjugated system means that the absorbed light has higher energy. Light having higher energy has a shorter wavelength.

Accordingly, the organic compound according to the present invention in the neutral state shows light absorption in the ultraviolet region, but does not show light absorption in the visible light region to show high transparency.

In addition, the organic compound in the oxidized state shows light absorption in the visible light region and is in the colored state. In contrast, the conductive polymer in the neutral state shows light absorption in the visible light region, and therefore, even in the oxidized state, "remnant" having an absorption band in the visible light region occurs in a portion where the electrochemical reaction is insufficient.

The organic compound according to the present invention, however, does not have an absorption band in the visible light region. Therefore, the organic compound can maintain high transparency, even if there is a portion where the electrochemical reaction is insufficient.

Since the compound of the present invention, however, has a π-conjugated system shorter than that of the conductive polymer, the stability of the radical cation of X serving as the core moiety is insufficient.

Accordingly, in the compound of the present invention, the phenyl groups linked to the thiophene skeleton or thiazole skeleton as the core moiety each have substituents at the ortho positions with respect to the core moiety.

The steric hindrance by the phenyl groups having bulky substituents protects the core moiety, which generates a radical cation.

The instability of the radical cation is caused by, for example, recombination between radicals due to high reactivity of the radical or hydrogen abstraction from other molecules by the radical. That is, the instability is caused by a reaction of a radical that has been brought into contact with other molecules.

Therefore, the steric hindrance by the phenyl groups having substituents at the ortho positions with respect to the core moiety highly enhances the stability of the radical cation by the steric hindrance groups preventing the core moiety from being brought into contact with other molecules.

Furthermore, the structure of each phenyl group (cage moiety) having the steric hindrance groups $A_1$ and $A_2$ protects the oxidation coloring moiety (core moiety) from attack by other substrates existing as, for example, other electrochromic material molecules or impurities. The cage moiety is required to have a molecular shape of enclosing the core moiety, and the phenyl groups are required to have substituents that are bulky as much as possible.

The solubility of the compound in a polar solvent can be increased by using polar substituents such as alkoxy groups as the steric hindrance groups $A_1$ and $A_2$. Accordingly, in particular, the steric hindrance groups can be polar substituents that are at least more bulky than a methoxy group.

The cage moiety according to the embodiment does not generate molecular conjugation with the core moiety. Whether molecular conjugation is generated or not is the boundary between the core moiety and the cage moiety.

In actual molecules, however, the molecular orbital is not completely interrupted because of fluctuation due to thermal motion or quantum-chemical fluctuation. In the embodiment, when the resonance is small, it is regarded that the molecular conjugation is not generated.

Since a smaller resonance between the core moiety and the cage moiety is advantageous, it is advantageous that the angle formed by the π electron orbitals of the core moiety and the cage moiety is approximately 90°.

Furthermore, in order to achieve the cage effect, the cage moiety has a structure in which the oxidation potential is relatively higher than that of the core moiety having a low oxidation potential so that the cage moiety is hardly oxidized.

It is believed that in such a configuration, the radical cation in the oxidized state is localized in the core moiety to block the core moiety from attack from the outside of the molecule by the shielding structure of the cage moiety, resulting in a remarkable improvement in stability of the radical cationic state.

The radical cation generated in the core moiety can be stabilized by increasing the electron density of the core moiety. It is therefore advantageous that the substituents $A_1$ and $A_2$ of the phenyl group in the cage portion have electron-donating properties. Examples of the substituent having a high electron-donating property and high steric hindrance include isopropoxy, t-butoxy, and ethylhexyloxy groups.

Specific structural formulae of the compounds according to the present invention are exemplified below, but the compounds according to the present invention are not limited thereto.

[Chem. 10]

A-1

A-2

A-3

A-4

A-5

A-6

[Chem. 11]

A-7

A-8

A-9

A-10

A-11

A-12

-continued

[Chem. 12]

A-13

A-14

A-15

A-16

A-17

-continued

A-18

[Chem. 13]

B-1

B-2

B-3

-continued

B-4

B-5

B-6

[Chem. 14]

B-7

-continued

B-8

B-9

B-10

[Chem. 15]

C-1

Among the exemplified compounds, in the compounds belonging to Group A, n in Formula [1] is an integer of 1; in the compounds belonging to Group B, n is an integer of 2; and in the compounds belonging to Group C, n is an integer of 3.

The structures represented by $A_1$ and $A_2$ are introduced into the ortho positions of each phenyl group and form skeletons to protect the thiophene skeleton or thiazole skeleton serving as the core moiety through the cage effect by the steric hindrance.

Accordingly, these organic EC compounds can have high durability against repetition of oxidation and reduction.

The organic compound of the present invention shows high stability against repetition of oxidation and reduction and discolors in the electrically neutral state and therefore can have high transparency that does not cause remnant in the visible light region.

When n in Formula [1] is an integer of 2 or more, the linking positions thereof are not particularly limited. For example, in the case of X representing a thiophene ring, the 2-position of one ring and the 5-position of another ring can be linked to each other. In the case of X representing a thiazole ring, similarly, the 2-position of one ring and the 5-position of another ring can be linked to each other.

The compound according to the present invention can be synthesized using the reactions shown by the following Formulae [5]. In the formulae, X represents a halogen atom. The compound can be synthesized by a coupling reaction catalyzed by a Pd catalyst using a combination of a halogenated core moiety compound (thiophene or thiazole derivative) and a boronic acid or boronic acid ester compound of a phenyl group having substituents at the ortho positions or a combination of a boronic acid or boronic acid ester compound of a core moiety compound and a halogenated phenyl group having substituents at the ortho-positions. As an example, a synthetic scheme when the core moiety is thiophene is shown in Formulae [5].

[Chem. 17]

The electrochromic material according to the present invention can be used in a known electrochromic device configuration. For example, an electrochromic device can be formed by disposed an electrochromic phase and an electrolyte layer between a pair of electrodes.

The electrochromic phase may be a solid phase formed by forming a film from the organic compound according to the present invention on an electrode or may be a solution phase formed by dissolving the organic compound according to the present invention in an electrolyte solution.

In the solid electrochromic phase, the film may be formed from the organic compound according to the present invention on an electrode substrate by any method, for example, by dissolving the compound in an appropriate solvent and applying it by a known coating method (e.g., spin coating, dipping, casting, an LB method, or an ink-jetting method), vacuum deposition, ionized deposition, sputtering, or plasma coating.

In the solution electrochromic phase, the organic compound according to the present invention and a supporting electrolyte are dissolved in an appropriate solvent (e.g., water or an organic polar solvent such as ethanol, propylene carbonate, ethylene carbonate, dimethyl sulfoxide, γ-butyrolactone, or acetonitrile), and the solution is injected between a pair of electrode substrates to form a device.

The EC device according to the embodiment may be formed by any method, for example, by injecting a solution containing the EC organic compound prepared in advance into the gap formed between a pair of electrode substrates by a vacuum injection, air injection, or meniscus method.

The EC device according to the embodiment can be used in an optical filter, a lens unit, or an image pickup apparatus.

The EC device according to the embodiment has high durability, shows high transparency in the bleached state, and shows rapid responses of coloring and discoloring. Accordingly, the device can be suitably used for controlling quantity of incident light to an image pickup element such as a camera or controlling incident wavelength distribution characteristics. The control of incident wavelength distribution is effective for color temperature conversion in image pickup.

That is, the quantity of light to be received by an image pickup device or the incident wavelength distribution characteristics can be controlled by installing the EC device in an optical path of an image pickup optical system (lens system) communicating with the image pickup device. The image pickup optical system is also referred to as a lens system, and an example thereof is a lens unit including a plurality of lenses.

The EC device according to the embodiment connected to a transistor functions as an optical filter. Examples of the transistor include TFTs and MIM elements.

The image pickup apparatus according to the embodiment includes an image pickup device and an image pickup optical system having an optical film. The EC device of the image pickup apparatus may be disposed at any position, i.e., may be disposed at any position in front of the image pickup system or in front of the image pickup device.

The EC device in the bleached state can exhibit high transparency to give a sufficient quantity of transmitted light with respect to incident light, and the EC device in the colored state can reliably shield the incident light to give modulated optical characteristics. In addition, the device shows excellent oxidation-reduction repeating characteristics to have a long operating life.

ADVANTAGEOUS EFFECTS OF INVENTION

The present invention can provide an electrochromic organic compound showing high stability against repetition of oxidation and reduction and high transparency in the bleached state without showing light absorption in the visible light region.

EXAMPLES

The present invention will be described more specifically by Examples, but is not limited thereto.

Example 1

Synthesis of Exemplary Compound A-6

[Chem. 18]

A-6

In a 50-mL reaction container, 241.9 mg (1.0 mmol) of XX-1 (2,5-dibromothiophene) and 753.1 mg (3.5 mmol) of 2-isopropoxy-6-methoxyphenylboronic acid were mixed in a toluene/tetrahydrofuran (4 mL/4 mL) solvent mixture, and dissolved oxygen was removed by nitrogen. Subsequently, 4.5 mg (0.02 mmol) of Pd(OAc)$_2$, 20.53 mg (0.05 mmol) of 2-dicyclohexylphosphino-2',6'-dimethoxybiphenyl (S-Phos), and 1162.4 mg (5.05 mmol) of tripotassium phosphate were added to the mixture under a nitrogen atmosphere, followed by heating to reflux at 110° C. for 8 hours. The reaction solution was cooled to room temperature, concentrated under reduced pressure, and subjected to silica gel chromatography (mobile phase: hexane/chloroform=1/4) for isolation and purification to give compound A-6 (362.8 mg, yield: 86.3%) as a white solid powder.

Mass-spectrometry (MS) and nuclear magnetic resonance spectrometry (NMR) of compound A-6 gave the results that the molecular weight and the ratio of integrated values of NMR peaks well agreed with the structure of compound A-6. Specifically, 412 as M$^+$ of this compound was confirmed by matrix-assisted laser desorption-ionization mass spectrometry (MALDI-MS). The measurement results of NMR are shown below:

$^1$H-NMR (CDCl$_3$) σ (ppm): 7.5 (s,2H), 7.17 (t,2H), 6.66 (d,2H), 6.63 (d,2H), 4.54 (sept,2H), 3.48 (s,6H), 1.32 (s,12H).

$^{13}$C-NMR (CDCl$_3$) σ (ppm): 158.27, 156.32, 134.26, 128.23, 128.06, 115.18, 108.30, 104.70, 71.78, 56.24, 22.49.

Example 2

Synthesis of Exemplary Compound A-11

[Chem. 19]

A-11

In a 50-mL reaction container, 500 mg (1.67 mmol) of XX-2 (2,5-dibromo-ethylenedioxythiophene) and 1.05 g (5.0 mmol) of 2-isopropoxy-6-methoxyphenylboronic acid were mixed in a toluene/tetrahydrofuran (10 mL/5 mL) solvent mixture, and dissolved oxygen was removed by nitrogen. Subsequently, 19 mg (0.083 mmol) of Pd(OAc)$_2$, 89 mg (0.22 mmol) of 2-dicyclohexylphosphino-2',6'-dimethoxybiphenyl (S-Phos), and 1.92 g (8.35 mmol) of tripotassium phosphate were added to the mixture under a nitrogen atmosphere, followed by heating to reflux at 110° C. for 7 hours. The reaction solution was cooled to room temperature, concentrated under reduced pressure, and subjected to silica gel chromatography (mobile phase: hexane/ethyl acetate=4/3) for isolation and purification to give compound A-11 (420 mg, yield: 54%) as a white solid powder.

As in Example 1, the structure of compound A-11 was confirmed by NMR and MALDI-MS. Specifically, 470 as M$^+$ of this compound was confirmed by MALDI-MS. The measurement results of NMR are shown below:

$^1$H-NMR (CDCl$_3$) σ (ppm): 7.21 (t,2H), 6.63 (d,2H), 6.60 (d,2H), 4.41 (m,2H), 4.20 (s,4H), 3.81 (s,6H), 1.25 (s,6H), 1.24 (s,6H).

$^{13}$C-NMR (CDCl$_3$) σ (ppm): 159.01, 157.52, 138.10, 129.20, 112.07, 108.96, 108.36, 104.53, 71.80, 64.49, 56.06, 22.23.

Example 3

Synthesis of Exemplary Compound A-18

A-18

In a 50-mL reaction container, 559.5 mg (1.13 mmol) of XX-3 and 771.0 mg (3.67 mmol) of 2-isopropoxy-6-methoxyphenylboronic acid were mixed in a toluene/tetrahydrofuran (6 mL/4 mL) solvent mixture, and dissolved oxygen was removed by nitrogen. Subsequently, 6.7 mg (0.03 mmol) of Pd(OAc)$_2$, 21.3 mg (0.052 mmol) of 2-dicyclohexylphosphino-2',6'-dimethoxybiphenyl (S-Phos), and 1166.2 mg (5.06 mmol) of tripotassium phosphate were added to the mixture under a nitrogen atmosphere, followed by heating to reflux at 110° C. for 8 hours.

The reaction solution was cooled to room temperature, concentrated under reduced pressure, and subjected to silica gel chromatography (mobile phase: hexane/ethyl acetate=4/1) for isolation and purification to give compound A-18 (545.8 mg, yield: 72.5%) as a white solid powder.

As in Example 1, the structure of compound A-18 was confirmed by NMR and MALDI-MS. Specifically, 664 as M$^+$ of this compound was confirmed by MALDI-MS. The measurement results of NMR are shown below:

$^1$H-NMR (CDCl$_3$) σ (ppm): 7.3 (t,2H), 6.62 (d,2H), 6.58 (d,2H), 4.48 (m,2H), 3.75 (s,6H), 2.51 (br,4H), 1.64 (m,4H), 1.56 (d,12H), 1.29-1.13 (m,20H), 0.81 (t,6H).

$^{13}$C-NMR (CDCl$_3$) σ (ppm): 160.89, 159.47, 157.61, 156.54, 130.33, 125.07, 110.58, 107.01, 103.68, 71.06, 56.06, 32.05, 30.36, 29.36, 29.28, 22.96, 22.43, 22.39, 14.46.

Example 4

Synthesis of Exemplary Compound B-7

B-1

In a 50-mL reaction container, 326.3 mg (1.01 mmol) of XX-4 (2,5-dibromobithiophene) and 749.8 mg (3.57 mmol) of 2-isopropoxy-6-methoxyphenylboronic acid were mixed in a toluene/tetrahydrofuran (4 mL/4 mL) solvent mixture, and dissolved oxygen was removed by nitrogen.

Subsequently, 5.9 mg (0.026 mmol) of Pd(OAc)$_2$, 21.4 mg (0.052 mmol) of 2-dicyclohexylphosphino-2',6'-dimethoxybiphenyl (S-Phos), and 1123.7 mg (4.88 mmol) of tripotassium phosphate were added to the mixture under a nitrogen atmosphere, followed by heating to reflux at 110° C. for 8 hours.

The reaction solution was cooled to room temperature, concentrated under reduced pressure, and subjected to silica gel chromatography (mobile phase: hexane/chloroform=1/3) for isolation and purification to give compound B-1 (418.8 mg, yield: 84.1%) as a white solid powder.

As in Example 1, the structure of compound B-1 was confirmed by NMR and MALDI-MS. Specifically, 494 as M$^+$ of this compound was confirmed by MALDI-MS. The measurement results of NMR are shown below:

$^1$H-NMR (CDCl$_3$) σ (ppm): 7.48 (d,2H), 7.18 (t,2H), 7.17 (d,2H), 6.65 (d,2H), 6.62 (d,2H), 4.58 (sept,2H), 3.87 (s,6H), 1.36 (s,12H).

$^{13}$C-NMR (CDCl$_3$) σ (ppm): 158.12, 156.14, 137.72, 133.35, 130.02, 128.42, 122.49, 114.24, 107.88, 104.54, 71.88, 56.27, 22.46.

Example 5

Synthesis of Exemplary Compound B-5

[Chem. 22]

In a 50-mL reaction container, 440.1 mg (1 mmol) of XX-5 and 751.1 mg (3.58 mmol) of 2-isopropoxy-6-methoxyphenylboronic acid were mixed in a toluene/tetrahydrofuran (4 mL/4 mL) solvent mixture, and dissolved oxygen was removed by nitrogen. Subsequently, 5.1 mg (0.023 mmol) of Pd(OAc)$_2$, 22.8 mg (0.056 mmol) of 2-dicyclohexylphosphino-2',6'-dimethoxybiphenyl (S-Phos), and 1193.1 mg (5.18 mmol) of tripotassium phosphate were added to the mixture under a nitrogen atmosphere, followed by heating to reflux at 110° C. for 8 hours.

The reaction solution was cooled to room temperature, concentrated under reduced pressure, and subjected to silica gel chromatography (mobile phase: hexane/ethyl acetate=4/3) for isolation and purification to give compound B-5 (177.3 mg, yield: 29.03%) as a white solid powder.

As in Example 1, the structure of compound B-5 was confirmed by NMR and MALDI-MS. Specifically, 610 as M$^+$ of this compound was confirmed by MALDI-MS. The measurement results of NMR are shown below:

$^1$H-NMR (CDCl$_3$) σ (ppm): 7.21 (t,2H), 6.61 (d,2H), 6.58 (d,2H), 4.43 (sept,2H), 4.14 (br,8H), 3.79 (s,6H), 1.24 (d,12H).

$^{13}$C-NMR (CDCl$_3$) σ (ppm): 159.52, 157.85, 138.58, 136.46, 129.74, 111.49, 108.52, 107.11, 104.46, 71.66, 65.21, 64.84, 56.43, 22.54.

Example 6

Synthesis of Exemplary Compound C-3

[Chem.23]

(1) In a 50-mL reaction container, 300 mg (1.24 mmol) of XX-1 and 1.10 g (3.72 mmol) of XX-6 were mixed in a toluene/tetrahydrofuran (8 mL/4 mL) solvent mixture, and dissolved oxygen was removed by nitrogen.

Subsequently, 8.4 mg (0.037 mmol) of Pd(OAc)$_2$, 40.7 mg (0.0992 mmol) of 2-dicyclohexylphosphino-2',6'-dimethoxybiphenyl (S-Phos), and 1.43 g (6.2 mmol) of tripotassium phosphate were added to the mixture under a nitrogen atmosphere, followed by heating to reflux at 110° C. for 7 hours.

The reaction solution was cooled to room temperature, concentrated under reduced pressure, and subjected to silica gel chromatography (mobile phase: hexane) for isolation and purification to give compound XX-7 (360 mg, yield: 70%) as a colorless viscous liquid.

(2) In a 100-mL reaction container, 355 mg (0.852 mmol) of XX-7 prepared in the above (1) was dissolved in 25 mL of N,N-dimethylformamide (DMF).

Subsequently, 333 mg (1.87 mmol) of N-bromosuccinimide was added to the solution, and the mixture was stirred at room temperature for 8 hours. Water was added to the reaction solution. After extraction with chloroform and washing with water, concentration under reduced pressure was performed to give compound XX-8 (470 mg, yield: 96%).

(3) In a 50-mL reaction container, 470 mg (0.818 mmol) of XX-8 and 515 mg (2.45 mmol) of 2-isopropoxy-6-methoxyphenylboronic acid were mixed in a toluene/tetrahydrofuran (5 mL/2.5 mL) solvent mixture, and dissolved oxygen was removed by nitrogen. Subsequently, 5.5 mg (0.0245 mmol) of Pd(OAc)$_2$, 27 mg (0.065 mmol) of 2-dicyclohexylphosphino-2',6'-dimethoxybiphenyl (S-Phos), and 942 mg (4.09 mmol) of tripotassium phosphate were added to the mixture under a nitrogen atmosphere, followed by heating to reflux for 7 hours. The reaction solution was cooled to room temperature, concentrated under reduced pressure, and subjected to silica gel chromatography (mobile phase: hexane/chloroform=1/2) for isolation and purification to give compound C-3 (520 mg, yield: 85%) as a light-yellow solid.

As in Example 1, the structure of compound C-3 was confirmed by NMR and MALDI-MS. Specifically, 744 as M$^+$ of this compound was confirmed by MALDI-MS. The measurement results of NMR are shown below:

$^1$H-NMR (CDCl$_3$) σ (ppm): 7.27 (t,2H), 7.06 (s,2H), 7.01 (s,2H), 6.62 (d,2H), 6.59 (d,2H), 4.43 (m,2H), 3.77 (s,6H), 2.31 (t,4H), 1.53 (m,4H), 1.32-1.10 (m,24H), 0.84 (t,6H).

$^{13}$C-NMR (CDCl$_3$) σ (ppm): 159.15, 157.53, 141.83, 136.37, 135.99, 129.51, 128.33, 124.36, 123.29, 112.85, 107.51, 103.63, 71.09, 55.86, 31.74, 29.97, 29.21, 29.11, 22.61, 22.13, 22.08, 14.13.

Example 7

Electrochromic Characteristics

The compounds shown in Examples 1 to 6 were dissolved in chloroform. The absorption spectra of the solutions in the neutral state (the bleached state) were measured with an ultraviolet and visible spectrophotometer (V-560, manufactured by JASCO Corp.).

Absorption spectra in the oxidized (colored) state were measured using a platinum working electrode, a platinum counter electrode, and a silver reference electrode. The compound of each Example was dissolved at a concentration of 5.0×10$^{-4}$ mol/L in a 0.1 mol/L solution of tetrabutylammonium perchlorate (supporting electrolyte) in dichloromethane, and changes in absorption spectrum and transmittance spectrum were measured by oxidizing the solution at a constant potential of not lower than the first oxidation potential of the compound to confirm the electrochromic characteristics.

The wavelength at the maximum absorption intensity in the measured absorption spectrum is shown in Table 1. In addition, the first oxidation potential E$_{1/2}$ (vs. Ag/Ag+) of each compound in the cyclic voltammetry (CV) of the above-mentioned solution is also shown.

TABLE 1

| Compound No. | λmax (nm) in the bleached state | λmax (nm) in the colored state | Oxidation potential E$_{1/2}$ (V) |
| --- | --- | --- | --- |
| A-6 | 321.0 | 505.0 | 0.67 |
| A-11 | 290.0 | 448.5 | 0.70 |

TABLE 1-continued

| Compound No. | λmax (nm) in the bleached state | λmax (nm) in the colored state | Oxidation potential E$_{1/2}$ (V) |
| --- | --- | --- | --- |
| A-18 | 358.0 | 405.0 | 1.04 |
| B-1 | 371.0 | 617.0 | 0.39 |
| B-5 | 361.0 | 545.0 | 0.35 |
| C-3 | 386.0 | 640.0 | 0.58 |

Figure 2:
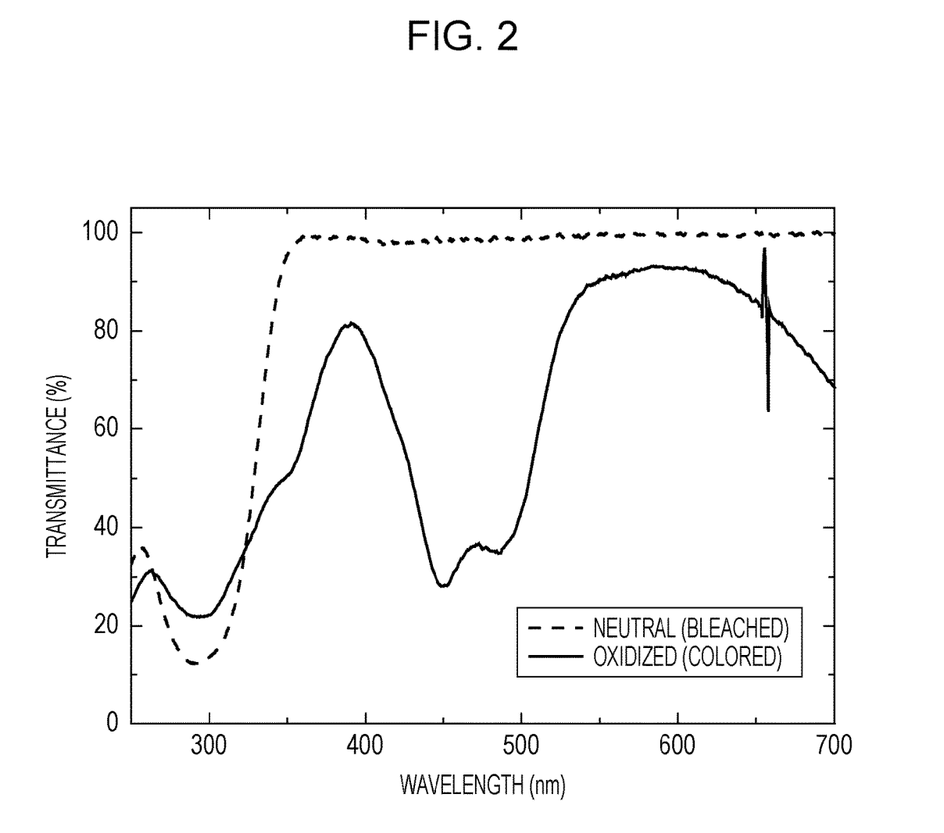
FIG. 2 shows ultraviolet and visible absorption spectra showing electrochromic characteristics of Exemplary Compound A-11 in Example 7.

As a typical example of these measurements, FIG. 2 shows transmittance spectra in the neutral and oxidized states of compound A-11.

In the neutral state of every compound, the maximum intensity of absorption peak λmax was observed in the ultraviolet region, and no absorption was observed over the entire visible light region. Thus, it was shown that the compounds were transparent materials.

In each compound, the type of color generated by oxidation showed the λmax in the visible light region, and coloring was confirmed by visual observation. The color in the oxidized state returned to the colorless transparent state by reduction. Thus, electrochromic characteristics upon oxidation-reduction were confirmed.

Example 8 and Comparative Example 1

Durable Stability in Oxidation-Reduction Cycle

Organic EC compounds A-6, A-11, A-18, B-1, B-5, and C-3 according to the present invention and a known compound Ref-1 as a comparative example were evaluated for durable stability against redox cycles. The compound Ref-1 as the comparative example is a known EC compound (diethyl viologen diperchlorate) that is colored in the reduced state. The structural formula of Ref-1 is shown below.

[Chem. 24]

Ref-1

2ClO$_4$$^-$

The durability was measured using a glassy carbon working electrode, a platinum counter electrode, and a silver reference electrode. Each sample solution was prepared by dissolving the compound of each Example at a concentration of 1.0×10$^{-4}$ mol/L in a 0.1 mol/L solution of tetrabutylammonium perchlorate (supporting electrolyte) in dichloromethane.

This solution was subjected to a square-wave potential program composed of oxidation at a constant potential of not lower than the oxidation potential of the compound for 10 seconds and reduction at a constant potential of 0 V (vs. Ag/Ag+) for 10 seconds for 10000 times. Changes in amount of oxidation peak current in cyclic voltammetry (CV) before and after the redox cycles for 10000 times are shown in Table 2 where Excellent means that the change is less than 20% and Poor means that the change is higher than 20%.

TABLE 2

| Compound No. | Durability evaluation |
| --- | --- |
| A-6 | Excellent |
| A-11 | Excellent |
| A-18 | Excellent |
| B-1 | Excellent |
| B-5 | Excellent |
| C-3 | Excellent |
| Ref-1 | Poor |

In compound Ref-1 of Comparative Example, the oxidation peak current amount was decreased by 20% after about 1600 times of the redox cycles to suggest deterioration, whereas in the compounds of Examples 1 to 6 according to the present invention, the changes in oxidation current amount were less than 20% even after 10000 times of the redox cycles to show stable redox cycles. The results that the organic compounds of the present invention show excellent durable stability against the oxidation-reduction cycles suggest that, compared with Ref-1 of Comparative Example, the bulky substituents of the cage moieties of the compounds of the present invention sterically protect the core moiety generating an unstable radical in the oxidized state. In the compounds of the present invention, the phenyl groups serving as the cage moieties have electron-donating alkoxy groups as substituents. This is believed to prevent the core moiety (radical cation) from side reaction and deterioration caused by electron deficiency in the oxidized state to enhance the durable stability.

As described above, the organic compound according to the present invention is a material that is transparent in the neutral state and shows high durability against oxidation-reduction repetition. The use of the compound in an EC device can provide stable characteristics, i.e., high transparency not showing light absorption in the visible light region in the bleached state and excellent durability.

The organic compound of the present invention shows high stability in oxidation-reduction repetition and also high transparency not showing light absorption in the visible light region in the bleached state and therefore can be applied to EC devices and also to optical filters, lens units, and image pickup apparatuses using the EC devices.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-286778, filed Dec. 27, 2011, which is hereby incorporated by reference herein in its entirety.

REFERENCE SIGNS LIST

11 ethylenedioxythiophene plane

12 phenyl group substituted by isopropoxy group and methoxy group

The invention claimed is:

1. An organic compound represented by Formula [1]:

in Formula [1], $A_1$ and $A_2$ are each independently selected from the group consisting of alkyl groups having 1 to 20 carbon atoms, alkoxy groups having 1 to 20 carbon atoms, and optionally substituted aryl groups, wherein each $R_1$ independently represents a hydrogen atom, a halogen atom, an alkyl group having 1 to 20 carbon atoms, an alkoxy group having 1 to 20 carbon atoms, an alkyl ester group having 1 to 20 carbon atoms, an optionally substituted aryl group, an optionally substituted amino group, or a cyano group, wherein the aryl group optionally has a substituent of an alkyl group having 1 to 4 carbon atoms;

n is an integer of 2 to 3; and each X is independently selected from the following Formulae [2] to [4], provided that X includes at least Formula [4]:

in Formulae [2] to [4], $R_2$, $R_3$, and $R_5$ are each independently selected from the group consisting of hydrogen atoms, halogen atoms, alkyl groups having 1 to 20 carbon atoms, alkoxy groups having 1 to 20 carbon atoms, optionally substituted aryl groups, alkyl ester groups having 1 to 20 carbon atoms, optionally substituted amino groups, and cyano groups; and $R_4$ represents an alkylene group having 1 to 20 carbon atoms.

2. The organic compound according to claim 1, wherein at least one of $A_1$ and $A_2$ is an alkoxy group having 1 to 20 carbon atoms.

3. The organic compound according to claim 2, wherein at least one of $A_1$ and $A_2$ is a methoxy group or an isopropoxy group.

4. An electrochromic device comprising;

a pair of electrode;

an electrochromic phase and an electrolyte disposed between the pair of electrode;

the electrochromic phase comprises the organic compound represented by Formula [1]:

[1]

in Formula [1], $A_1$ and $A_2$, are each independently selected from the group consisting of alkyl groups having 1 to 20 carbon atoms, alkoxy groups having 1 to 20 carbon atoms, and optionally substituted aryl groups, wherein each $R_1$ independently represents a hydrogen atom, a halogen atom, an alkyl group having 1 to 20 carbon atoms, an alkoxy group having 1 to 20 carbon atoms, an alkyl ester group having 1 to 20 carbon atoms, an optionally substituted aryl group, an optionally substituted amino group, or a cyano group, wherein the aryl group optionally has a substituent of an alkyl group having 1 to 4 carbon atoms;

n is an integer of 2 to 3; and each X is independently selected from the following Formulae [2] to [4], provided that X includes at least

Formula [4]:

[2]

[3]

[4]

in Formulae [2] to [4], $R_2$, $R_3$, and $R_5$ are each independently selected from the group consisting of hydrogen atoms, halogen atoms, alkyl groups having 1 to 20 carbon atoms, alkoxy groups having 1 to 20 carbon atoms, optionally substituted aryl groups, alkyl ester groups having 1 to 20 carbon atoms, optionally substituted amino groups, and cyano groups; and $R_4$ represents an alkylene group having 1 to 20 carbon atoms.

5. The electrochromic device according to claim 4, wherein the electrochromic phase is solution phase.

6. An optical filter comprising the electrochromic device according to claim 4 and a transistor connected to the electrochromic device.

* * * * *